United States Patent [19]

Dockner et al.

[11] Patent Number: 4,973,751

[45] Date of Patent: Nov. 27, 1990

[54] PREPARATION OF UNSATURATED COMPOUNDS BY ELIMINATION REACTION

[75] Inventors: Toni Dockner, Meckenheim; Eckhard Hickmann, Dannstadt-Schauernheim; Herbert Krug, Ludwigshafen, all of Fed. Rep. of Germany

[73] Assignee: BASF Aktiengesellschaft, Ludwigshafen, Fed. Rep. of Germany

[21] Appl. No.: 275,663

[22] Filed: Nov. 22, 1988

Related U.S. Application Data

[63] Continuation of Ser. No. 129,355, Nov. 30, 1987, abandoned, which is a continuation of Ser. No. 826,760, Feb. 6, 1986, abandoned.

[51] Int. Cl.$^5$ ............................. C07C 103/127
[52] U.S. Cl. .................................... 504/215
[58] Field of Search ............................ 564/215

[56] References Cited

U.S. PATENT DOCUMENTS

| | | | |
|---|---|---|---|
| 2,667,517 | 1/1954 | Longley | 568/691 |
| 2,962,534 | 11/1960 | Montagna et al. | 568/691 |
| 3,377,340 | 4/1968 | Hartwimmer et al. | 564/215 |
| 3,914,304 | 10/1975 | Schnabel et al. | 564/215 |
| 4,322,271 | 3/1982 | Jensen et al. | 564/215 |
| 4,334,097 | 6/1982 | Schmidt | 564/215 |
| 4,469,887 | 9/1984 | Brockhaus et al. | 568/691 |
| 4,567,300 | 1/1986 | Murao et al. | 564/215 |
| 4,578,515 | 3/1986 | Dawson et al. | 564/215 |

FOREIGN PATENT DOCUMENTS

| | | |
|---|---|---|
| 1444454 | 7/1976 | United Kingdom . |
| 2091259 | 7/1982 | United Kingdom . |

OTHER PUBLICATIONS

Patent Abstracts of Japan, vol. 8, No. 218(C-245)(1655), Oct. 4, 1984–Preparation of Unsaturated Carbonyl Compound. -59-104338 (A).

Shono et al., J. Amer. Chem. Soc., 104, 6697 (1982).

Nyberg, Synthesis, 1976, 545.

C. H. DePuy and R. W. King Chem. Rev., 60, 431 (1960).

The Chemistry of the Ether Linkage (1967) Interscience Publishers, New York, ed. Saul Patai, p. 337.

*Primary Examiner*—Nicky Chan
*Attorney, Agent, or Firm*—Keil & Weinkauf

[57] ABSTRACT

Compounds of the formula I

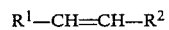

$$R^1-CH=CH-R^2 \qquad I$$

where $R^1$ is hydrogen or alkyl and $R^2$ is alkoxy or acylamino, and $R^1$ and $R^2$ together may form a heterocyclic ring, are prepared by elimination of the radical $R^3OH$ from a compound of the formula II

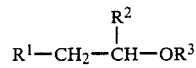

$$R^1-CH_2-\overset{\overset{\displaystyle R^2}{|}}{CH}-OR^3 \qquad II$$

where $R^1$ and $R^2$ have the above meanings and $R^3$ is alkyl, by a method in which the elimination is carried out by passing the compound of the formula II in a liquid or gaseous state into a high-boiling mineral oil above the boiling point of compound I being formed, compound I is taken off in gaseous form, and the high-boiling mineral oil enriched with by-products is removed and replaced with fresh mineral oil.

5 Claims, 1 Drawing Sheet

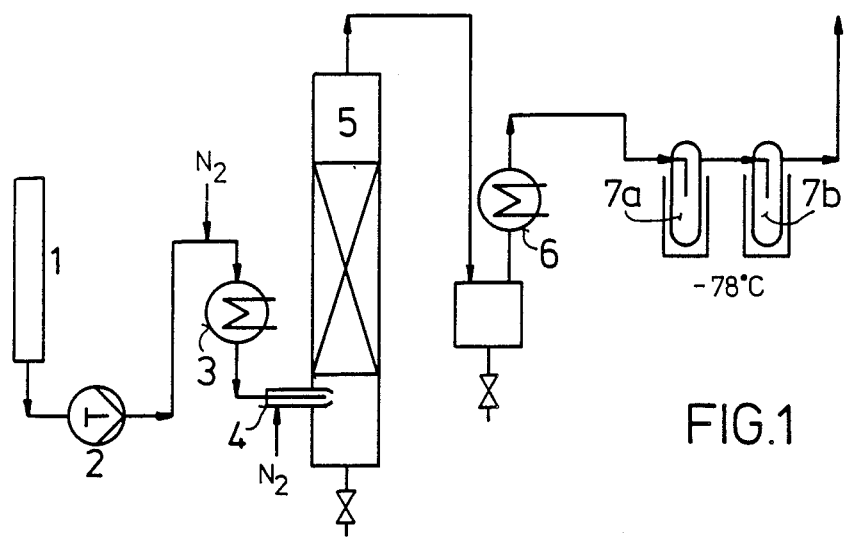
FIG.1
FIG.2
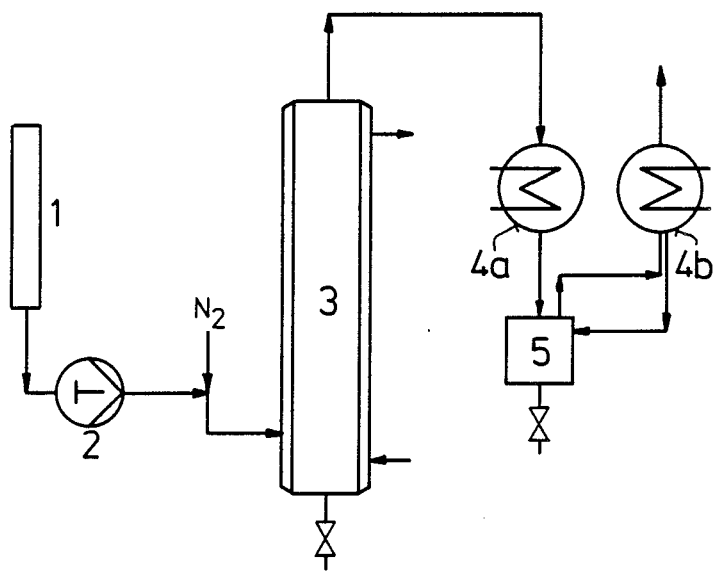

PREPARATION OF UNSATURATED COMPOUNDS BY ELIMINATION REACTION

This application is a continuation of application Ser. No. 129,355, filed on Nov. 30, 1987, abandoned, which is a continuation of Ser. No. 826,760, filed on Feb. 6, 1986, abandoned.

The present invention relates to a process for the preparation of unsaturated compounds by an elimination reaction from an acetal or α-alkoxyamide in the liquid phase in a high-boiling mineral oil, the mineral oil being replaced with fresh mineral oil, and the mineral oil enriched with by-products being fed for incineration.

In the presence of strong acids, for example, an alcohol can frequently be eliminated from an acetal in the liquid phase, in a very smooth reaction. To do this, high concentrations of a strong acid, such as sulfuric acid or phosphoric acid, are required in order to achieve adequate reaction rates. The elimination reaction takes place as a rule at from 180° to 200° C. in the liquid phase. Because of these drastic conditions, substantial amounts of by-products are formed, for example by etherification, isomerization and polymerization of the resulting olefin.

It is an object of the present invention to provide a process which does not possess the stated disadvantages and permits the by-products to be separated off in a simple manner.

We have found that this object is achieved, according to the invention, by a process for the preparation of compounds of the formula I

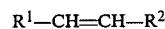
$$R^1-CH=CH-R^2 \qquad I$$

where $R^1$ is hydrogen or alkyl and $R^2$ is alkoxyamino or acylamino, and $R^1$ and $R^2$ together may form a heterocyclic ring, by eliminating the radical $R^3OH$ from a compound of the formula II

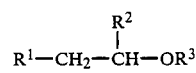
$$R^1-CH_2-\overset{R^2}{\underset{|}{CH}}-OR^3 \qquad II$$

where $R^1$ and $R^2$ have the above meanings and $R^3$ is alkyl, if the elimination reaction is carried out by passing a compound of the formula II in the liquid or gaseous state into a high-boiling mineral oil at above the boiling point of the compound I being formed, the compound I is taken off in gaseous form, and the high-boiling mineral oil enriched with by-products is removed and replaced with fresh mineral oil.

Particularly suitable compounds of the formula II are acetals and α-alkoxyamides in which $R^1$ is hydrogen or an aliphatic radical of 1 to 20, preferably 1 to 10, carbon atoms, and $R^2$ is unsubstituted or substituted alkoxy of 1 to 20, preferably 1 to 10, carbon atoms, or is acylamino of 1 to 20, preferably 1 to 10, carbon atoms which is unsubstituted or additionally substituted at the nitrogen atom by alkyl, aralkyl or aryl, or in which $R^1$ and $R^2$ together form an unsubstituted or substituted oxygen-containing or nitrogen-containing heterocyclic structure, and in which $R^3$ is an aliphatic radical of 1 to 20, preferably 1 to 10, carbon atoms.

Specific examples of suitable starting compounds II are open-chain acetals, such as acetaldehyde dimethyl acetal, propionaldehyde dimethyl acetal, propionaldehyde diethyl acetal or isobutyraldehyde dimethyl acetal, cyclic acetals, such as 2,5-dimethoxy-2,5-dihydrofuran and in particular 3-formyl-2,5-dimethoxy-2,5-dihydrofuran, and α-alkoxyamides, such as α-methoxy-, α-ethoxy- or α-isopropoxyethylformamide, α-methoxyethyl-ethylformamide or α-methoxyethyl-methylacetamide.

For the purposes of the present invention, high-boiling mineral oils are high-boiling refinery products having a boiling point >150° C., such as gas oil, vacuum gas oil, heavy fuel oil, industrial white oil, molten paraffin wax and aromatic hydrocarbon oil. Vacuum gas oil having a boiling point greater than 200° C., in particular boiling within a range from 350° to 500° C., is advantageously used.

Depending on the type of reaction, the elimination reaction can be carried out with or without catalyst, although a catalyst is preferably employed. Where catalysts are used, it is possible to employ one which is either insoluble or soluble in the mineral oil, the catalyst accordingly being dissolved, emulsified or suspended in the mineral oil.

Preferably, acidic catalysts, such as aliphatic or aromatic sulfonic acids, e.g. benzenesulfonic acid, toluenesulfonic acid or dodecylbenzenesulfonic acid, sulfuric acid and halfesters of sulfuric acid, such as alkylsulfuric acid, phosphoric acid and its partially esterified derivatives, and boric acid and its acidic derivatives, are preferably used. Anhydrides, such as phosphorus pentoxide, sulfur dioxide and boron oxide, may also be used.

The catalysts which are soluble in the mineral oil are generally added in amounts of from 0.01 to 25, preferably from 0.1 to 10, in particular from 0.5 to 5, % by weight, based on the mineral oil.

Suitable suspended catalysts are alumina, aluminum phosphate, boron phosphate, aluminum silicate, silica gel, titanium oxide, heteropolyacids of phosphorus, and molybdic and tungstic acid.

The elimination reaction is generally carried out at from 50° to 600° C., preferably from 50° to 550° C., in particular from 150° to 350° C., under atmospheric or superatmospheric pressure. However, it is also possible to employ reduced pressure.

Examples of suitable reactors for the elimination reaction are stirred kettles. However, vertical cylindrical reactors, such as bubble tray columns, bubble columns, or packed columns, are advantageously used for the novel process. The starting material or materials are as a rule fed in as a gas or liquid at the bottom of the reactor filled with mineral oil. It may be advantageous to dilute the vaporized starting material in an inert gas, examples of suitable inert gases being steam, carbon dioxide and, preferably, nitrogen.

The reaction products are removed in gaseous form from the top of the reactor and are then advantageously condensed. Condensation may be followed by a further purification stage, for example distillation or fractionation.

The process can be carried out batchwise or continuously, the continuous procedure being preferred. In the latter procedure, it may be advantageous to feed in and remove the mineral oil continuously, for example where the reaction in question is one in which cracked products are formed. These cracked products are discharged continuously from the reactor, together with the mineral oil. As a rule, it is not economical to work up and recycle the mineral oil removed since the mineral oil is as a rule cheaply available, for example as fuel oil or vacuum gas oil. Advantageously, therefore, the mineral oil removed, which contains cracked products, is fed for incineration, and fresh mineral oil is introduced into the reactor.

The novel process has substantial advantages over the prior art one:

Catalytic amounts of acid are sufficient or cleavage can be carried out by a purely thermal reaction, and the reaction temperature is in general 50°–100° C. lower than in the elimination reaction over a heterogeneous catalyst in the gas phase. Polymers, cracked products and fairly high-boiling by-products remain in the mineral oil, which need not be regenerated and is advantageously fed to a power station, if necessary after the catalyst has been separated off. In the dehydration in the oil bed, isomerization reactions do not take place to any significant degree if at all, and the yields are higher. Furthermore, the process is substantially more economical to carry out industrially than are gas phase reactions over heterogeneous catalysts, as described in a large number of publications and also carried out in practice. Finally, incineration of the reaction medium and the by-products and cracked products present therein results in less environmental pollution.

IN THE DRAWING

FIG. 1 is a schematic view of one apparatus that can be used in carrying out the process; and FIG. 2 is a schematic view of a second suitable apparatus.

The Examples which follow illustrate the invention. Parts bear the same relation to parts by volume as that of the kilogram to the liter.

EXAMPLE 1

In an apparatus as shown in FIG. 1, 66 parts/hour of propionaldehyde diethyl acetal are metered from a stock vessel 1 by means of a metering pump 2, mixed with 6,000 parts by volume/hour of nitrogen and then fed into a vaporizer 3 heated at 120° C. From this vaporizer, it passes in gaseous form via a two-material nozzle 4, together with a further 6000 parts by volume/hour of nitrogen, into a reactor 5 which contains 1700 parts of vacuum gas oil and is heated at 245° C. The reactor is a glass tube which is provided with a jacket, has a length of 1300 mm and a diameter of 60 mm and is ⅔ full with 15 mm Pall rings. The vacuum gas oil contains 5% by weight of dodecylbenzenesulfonic acid as a catalyst. The vapors leaving the reactor are condensed in a condenser 6 and in cold traps 7a and 7b. 63 parts/hour of condensate containing 2.1% by weight of unconverted acetal, 46.8% by weight of ethyl prop-1-enyl ether and 34% by weight of ethanol are obtained. This corresponds to a conversion of 98%. The yield of ether is 70% of theory, based on converted acetal.

EXAMPLE 2

The procedure described in Example 1 is followed, except that 52 parts of propionaldehyde dimethyl acetal are used. 48 parts/hour of condensate containing 21.7% by weight of unconverted acetal, 42% by weight of methyl prop-1-enyl ether and 18.7% of methanol are obtained. This corresponds to a conversion of 80% and a yield of 70% of theory, based on converted acetal.

EXAMPLE 3

In an apparatus as described in FIG. 2, 72 parts/hour of 2,5-dimethoxy-3-formyltetrahydrofuran are fed from vessel 1 by means of metering pump 2, together with 200 parts by volume/hour of nitrogen, in liquid form via a capillary tube into reactor 3. The reactor consists of a jacketed tube having a length of 1.25 m and a diameter of 60 mm, and does not contain any baffles or packing. The reactor is filled with 1700 parts of vacuum gas oil (bp. >350° C.) and contains 1% by weight of dodecylbenzenesulfonic acid as catalyst, and the reaction temperature is 180° C. The vapors leaving the reactor are condensed in condensers 4a and 4b and collected in discharge vessel 5. In order to discharge the resulting by-products, e.g. polymers, from the reactor, 100 parts/hour of vacuum gas oil are discharged through the outlet valve in the bottom, and replaced by 100 parts/hour of fresh oil containing the catalyst. 59.1 parts/hour of a mixture containing 52.1% by weight of 3-formylfuran, 43.2% by weight of methanol, 1.3% by weight of 2,5-dimethoxy-3-formyltetrahydrofuran and 3% by weight of 3-formylfuran dimethyl acetal are discharged. This corresponds to a conversion of 99% and a yield of 72%, based on the conversion, of 3-formylfuran.

The 3-formylfuran formed can be obtained in a purity of 96–98% having a boiling point of 45° C./10 by fractional distillation.

COMPARATIVE EXAMPLE (to Example 3)

In an attempt to prepare 3-formylfuran from 2,5-dimethoxy-3-formyltetrahydrofuran in an acid-catalyzed reaction using inorganic acids (e.g. sulfuric acid, phosphoric acid or acidic silica gel) or organic acids (e.g. p-dodecylbenzenesulfonic acid or 2-ethylhexanoic acid), with elimination of methanol, the major part of the starting material was converted to a resin in an exothermic reaction. The maximum yield of 3-formylfuran achievable was about 5% of theory.

EXAMPLES 4 to 6

An α-alkoxyethyl-ethylformamide of the general formula

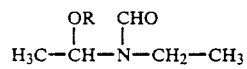

is added dropwise, in the course of about 3–5 hours and while about 20 parts by volume of nitrogen are passed through, to a mixture of high-boiling liquid paraffin (white oil) and 1% of p-dodecylbenzenesulfonic acid, which is heated at about 190° C. The starting material is completely converted, and a mixture of vinylethylformamide and the relevant alcohol ROH distills off. This mixture is condensed and redistilled to give 98.5–99.5% pure vinylethylformamide.

| Example | α-Alkoxyethyl-ethylformamide R/[parts] | White oil [parts by volume] | p-Dodecyl-benzene-sulfonic acid [parts] | Yield of vinylethyl-formamide [parts]/% of theory |
|---|---|---|---|---|
| 4 | CH₃/786 | 400 | 8 | 534/90 |
| 5 | CH₂H₅/145 | 400 | 1.5 | 91/91 |
| 6 | i-C₃H₇/79.5 | 400 | 0.9 | 48/97 |

COMPARATIVE EXAMPLE (to Example 6)

(similar to J. Amer. Chem. Soc. 104 (1982), 6697 and Synthesis 1976, 545)

A mixture of 80 parts of α-isopropoxyethyl-ethyl-formamide and 8 parts of ammonium chloride was heated at 140°–155° C. for about 2.5 hours while nitrogen was passed through. During this procedure, 24 parts of low boilers (containing isopropanol) distilled off. Distillation of the crude reaction product gave 34 parts of ethylformamide (identified by comparing gas chromatographic data with the corresponding data for authentic ethylformamide, appropriate elemental analysis and NMR spectrum), while 29 parts of non-distillable residue remained behind.

We claim:

1. A process for the preparation of a compound of the formula I $$R^1-CH=CH-R^2 \qquad I$$

where $R^1$ is hydrogen or alkyl and $R^2$ is acylamino, by elimination of the radical $R^3OH$ from a compound of the formula II $$R^1-CH_2-\underset{\underset{OR^3}{|}}{\overset{R^2}{C}}H \qquad II$$

where $R^1$ and $R^2$ have the above meanings and $R^3$ is alkyl, wherein the elimination reaction is carried out by passing the compound of the formula II in a liquid or gaseous state into a high-boiling mineral oil at above the boiling point of the compound I being formed and at a temperature of from 150° to 350° C., compound I is taken off in gaseous form, and the high-boiling mineral oil enriched with by-products is removed and replaced with fresh mineral oil.

2. The process of claim 1, wherein the mineral oil enriched with by-products is fed for incineration.

3. The process of claim 1, wherein the high-boiling mineral oil used in gas oil, vacuum gas oil, heavy fuel oil, industrial white oil or a vacuum residue.

4. The process of claim 1, wherein the elimination reaction is carried out over a dehydration catalyst.

5. The process of claim 1, wherein the elimination reaction is carried out by a continuation procedure.

* * * * *

UNITED STATES PATENT AND TRADEMARK OFFICE
CERTIFICATE OF CORRECTION

PATENT NO. : 4,973,751

DATED : November 27, 1990

INVENTOR(S) : Toni DOCKNER et al.

It is certified that error appears in the above-identified patent and that said Letters Patent is hereby corrected as shown below:

ON THE TITLE PAGE:

please insert --Foreign Application Priority Data

March 2, 1985...Fed. Rep. of Germany   DE   ...3507378--

Signed and Sealed this

Eleventh Day of August, 1992

*Attest:*

DOUGLAS B. COMER

*Attesting Officer*      *Acting Commissioner of Patents and Trademarks*